United States Patent [19]

Esser et al.

[11] Patent Number: 4,887,612

[45] Date of Patent: Dec. 19, 1989

[54] ENDOSCOPIC BIOPSY FORCEPS

[75] Inventors: Theodor Esser, Stony Brook; Thomas E. Doherty, Setauket, both of N.Y.

[73] Assignee: Esco Precision, Inc., Stony Brook, N.Y.

[21] Appl. No.: 186,564

[22] Filed: Apr. 27, 1988

[51] Int. Cl.⁴ .............................................. A61B 10/00
[52] U.S. Cl. .................................. 128/751; 128/749; 294/116; 606/208; 606/174
[58] Field of Search ................. 128/4, 303 R, 303.15, 128/305, 321, 345, 749, 751, 5–10; 604/22; 294/115, 116; 81/128

[56] References Cited

U.S. PATENT DOCUMENTS

| 2,034,785 | 3/1936 | Wappler . | |
|---|---|---|---|
| 3,840,003 | 10/1974 | Komiya . | |
| 3,895,636 | 7/1975 | Schmidt | 128/321 |
| 3,943,916 | 3/1976 | Vadas . | |
| 3,964,468 | 6/1976 | Schulz . | |
| 4,038,987 | 8/1977 | Komiya | 128/321 |
| 4,151,763 | 5/1979 | Colvin | 81/128 |
| 4,171,701 | 10/1979 | Walter et al. | 128/354 |
| 4,572,185 | 2/1986 | Rich | 128/321 |
| 4,646,751 | 3/1987 | Maslanka . | |
| 4,655,219 | 4/1987 | Petruzzi . | |
| 4,662,374 | 5/1987 | Blake, III | 128/321 |
| 4,669,471 | 6/1987 | Hayashi . | |
| 4,721,116 | 1/1988 | Schintgen et al. | 128/305 |

Primary Examiner—Michael H. Thaler
Assistant Examiner—William Lewis
Attorney, Agent, or Firm—Scully, Scott, Murphy & Presser

[57] ABSTRACT

An endoscopic biopsy forceps device incorporating a novel and unique camming arrangement for selectively opening and closing the biopsy cutting jaws of the biopsy forceps which will render the entire device of a simpler construction and reliable in operation, while concurrently making it considerably less expensive to produce.

7 Claims, 2 Drawing Sheets

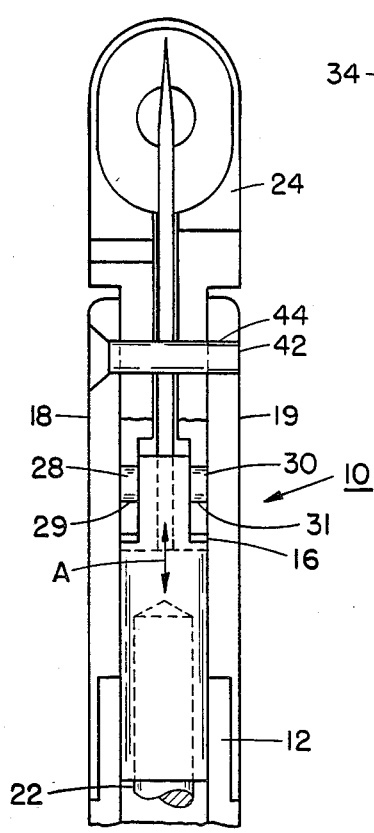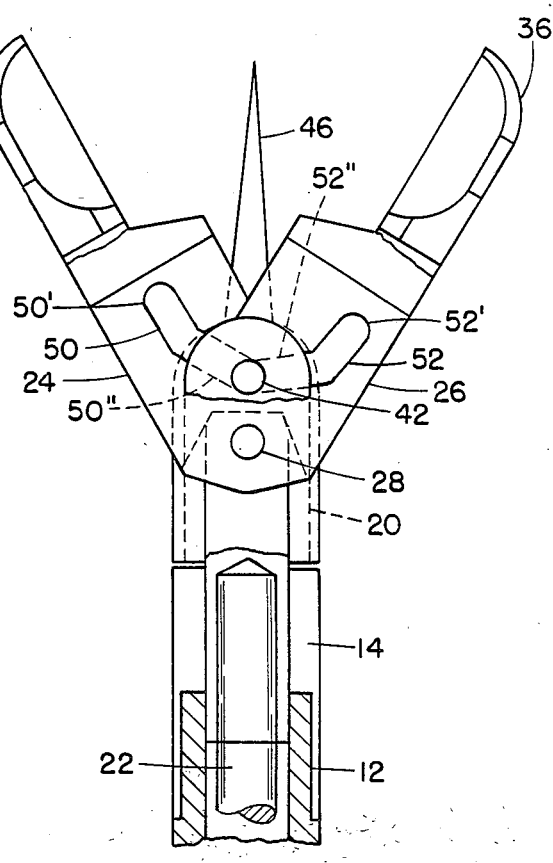
FIG.3
FIG.4

ENDOSCOPIC BIOPSY FORCEPS

BACKGROUND OF THE INVENTION

1. Field of the Invention

The present invention relates to biopsy forceps and, more particularly, relates to an endoscopic biopsy forceps device incorporating a novel and unique camming arrangement for selectively opening and closing the biopsy cutting jaws of the biopsy forceps which will render the entire device of a simpler construction and reliable in operation, while concurrently marking it considerably less expensive to produce.

Although varied types of biopsy forceps are currently in widespread use, such as in conjunction with endoscopic purposes, these are generally of complicated constructions necessitating the manufacture and assembly of numerous, highly precise components and, as a consequence, are quite expensive. Ordinarily, an endoscopic biopsy forceps device must be sterilized in strict compliance with rigid medial standards after each use thereof with a patient, so as to enable the device to again be safely employed with another patient for subsequent medical and/or surgical endoscopic biopsy procedures. Such sterilizing procedures entail immersing and rinsing the contaminated endoscopic biopsy forceps devices in a suitable chemical sterilizing solutions and/or subjecting the biopsy devices to sterilizing in an autoclave. The sterilizing of the biopsy devices with the utilization of chemical sterilizing solutions has, in more recent years, given rise to concerns that the contaminated biopsy devices were not adequately sterilized for reuse with other patients, particularly in view of the considerable dangers to patients through exposure to potentially serious and even life-threatening infection with the AIDS virus (Acquired Immunity Deficiency Syndrome) or hepatitis B viruses, wherein sterilizing of the devices by means of such chemical solutions may not always be adequate to destroy the viruses, or at the very least, raise doubts as to the efficacy of the solutions. Furthermore, subjecting currently utilized endoscopic biopsy forceps devices to sterilizing procedures in an autoclave, under extremely rigorous physical conditions, frequently causes the rather delicate biopsy forceps devices to be destroyed, or damaged and warped to such an extent as to render the devices unusable for repeated applications.

In order to overcome the limitations and drawbacks which are currently encountered in the technology, and particular in endoscopy, with respect to the constructions and employment of endoscopic biopsy forceps which will meet with the requirements of the medical profession, the present invention contemplates the provision of an endoscopic biopsy forceps device which, to an appreciable and highly desirably extent, reduces the large number of components in each such device; and in particular, affords for a considerable reduction in the necessary articulated elements, pivot points, rivets and attendant riveting operations in assembling the forceps device. In view of the complex construction of such prior art biopsy forceps devices are extremely expensive, and because it may not always be possible to properly sterilize the device to provide adequate safeguards against infections for patients exposed to previously used devices, rendering discarding thereof uneconomical, and possibly subjecting the medical facility and/or staff to legal liabilities in the event a patient is infected by a contaminated device.

2. Discussion of the Prior Art

Among the typical types of endoscopic biopsy forceps and similar types of devices which are currently known, the following are considered to be representative of the state-of-the-technology.

Komiya U.S. Pat. No. 4,038,987 discloses a forceps device for an endoscope, wherein the operation of the cutting jaws of the forceps are effectuated through the intermediary of a toggle joint which is articulated by a control wire through the interposition of suitable linkage components. The toggle mechanism provided for in this patent necessitates the utilization of separate pivot pins for each forceps jaw and provides for the type of operation in which the least amount of mechanical advantage is applied to the jaws during the closing of the forceps. This structure utilizes a multiplicity of linkage elements and pivots, rendering it highly susceptible to damage during sterilizing, while the device is extremely expensive because of the numerous components employed therein, necessitating the repeated use thereof in order to cause the device to be economical.

Blake, III, U.S. Pat. No. 4,662,374 discloses a ligator device in which a cam track is employed as a so-called "time delay" for the retraction of the clips proximate one of the clamping jaws. The operation of the camming arrangement utilized in Blake is completely unlike that of the camming arrangement utilized in the inventive endoscopic biopsy forceps and, moreover, necessitates the incorporation of an additional toggle mechanism in order to actuate the movement of the jaws. This particular device would not be employable as an endoscopic biopsy forceps.

Rich U.S. Pat. No. 4,572,185 employs a movable pin engaging a cam track in an operative mode as described hereinabove with respect to Blake, and necessitates the incorporation of a secondary pin as a pivot for the jaws of a surgical needle holder. This structure requires a more complex pin and cam track arrangement in comparison with the inventive endoscopic biopsy forceps device, and necessitates the utilization of auxiliary components which render the structure thereof expensive and inapplicable to a simple biopsy forceps device as is contemplated by the present invention.

Walter, et al. U.S. Pat. No. 4,171,701 primarily pertains to a camming structure incorporated into a tweezer device, which requires the use of secondary pin and linkage components in order to actuate the jaws of the device, and is not at all suggestive of the simple, reliable and inexpensive camming arrangement employed in conjunction with the inventive endoscopic biopsy forceps device.

Further types of biopsy forceps and the like, all of which employ relatively complex pivot points, linkages and toggle mechanisms, are respectively disclosed in Komiya U.S. Pat. No. 3,840,003; Hayashi U.S. Pat. No. 4,669,471; Maslamka U.S. Pat. No. 4,646,751; and Schmidt U.S. Pat. No. 3,895,636. The constructions disclosed therein are primarily of the complex pivot pin and linkage systems, also employing toggle linkages and parallelogram linkages, which render the devices extremely complex, expensive and not at all adapted for single use or so-called throw-away operation as contemplated by the invention.

SUMMARY OF THE INVENTION

Accordingly, in order to eliminate or ameliorate the disadvantages and drawbacks encountered in prior art biopsy forceps, particularly those employed in endoscopy, the present invention relates to a unique and novel endoscopic biopsy forceps device inexpensively constituted from only a few and simple parts, wherein the usual types of linkages and number of pivot points required for the articulation of the forceps jaws have been extensively eliminated or reduced, and replaced by a simple camming arrangement in the form of cam tracks which, nevertheless, results in a highly reliable and simply operated endoscopic biopsy forceps device. This novel structure extensively reduces the production costs of the forceps device to such an extent in comparison with the more complex prior art devices, such as to enable the device to be economically employed and discarded after only a single use; in essence, causing the device to become an inexpensive, disposable or so-called "throw-away" endoscopic biopsy forceps. This eliminates the necessity for having to subject the endoscopic biopsy forceps device to sterilizing in a chemical solution and/or an autoclave, and completely eliminates the danger of possible infection of a patient by a previously used and sterilized, but possibly still contaminated forceps device.

In order to achieve the foregoing object, the inventive endoscopic biopsy forceps device incorporates a novel camming arrangement comprising cooperating cam tracks formed in each of the shank portions of the cooperating forceps levers which cam tracks are displaceable along the surface a stationary guide or cam pin extending therethrough, and which is fastened to a housing attached to a flexible sheath which, in turn, is connected to an operating handle for the endoscope. The levers of the endoscopic biopsy forceps are articulated to a member which is slidable within a housing fastened to the end of the flexible sheath, the slidable member being reciprocated by a wire extending within the sheath, causing the cam tracks to move along the stationary pivot pin such as to in view of their curvatures or shapes, respectively, open or close clamping jaws on the forceps levers. This construction reduces the number of pivot points encountered in prior art devices, and reduces the linkage components and pivots required by more than one-half in comparison with those of the currently known endoscopic biopsy forceps devices.

Pursuant to a preferred embodiment of the invention, the stationary pivot or pin along which the cam tracks are movable may be in the form of a screw extending through and fastened to the housing, thereby eliminating the necessity for welding and/or riveting of a pivot pin, and even further increasing the reliability and reducing the cost of the biopsy forceps device.

In accordance with a modification of the invention, the cam tracks may be of a linearly-angled slot configuration so as to impart the greatest clamping force to the jaws upon closing thereof.

Accordingly, it is an object of the present invention to provide a novel endoscopic biopsy forceps device which incorporate a camming arrangement for securely opening and closing the clamping jaws of the forceps.

It is another object of the present invention to provide an endoscopic biopsy forceps of the type described herein, in which the device eliminates toggle linkages and pivot points and renders the construction thereof extremely simple with a few as possible operating components.

Yet another object of the present invention is to provide an endoscopic biopsy forceps device in which the pivot for the levers and jaws of the forceps device comprises a stationary screw member having the cam tracks articulated there along for actuating the levers of the forceps.

BRIEF DESCRIPTION OF THE DRAWINGS

Reference may now be had to the following detailed description of exemplary embodiments of the invention showing preferred constructions for the inventive endoscopic biopsy forceps device; taken in conjunction with the accompanying drawings; in which:

FIG. 3 illustrates a sectional view through the device taken along line 3—3 in FIG. 2; and FIG. 4 illustrates a second embodiment of the endoscopic biopsy forceps device similar to FIG. 1 but with a modified cam track configuration.

DETAILED DESCRIPTION

Figure 1:
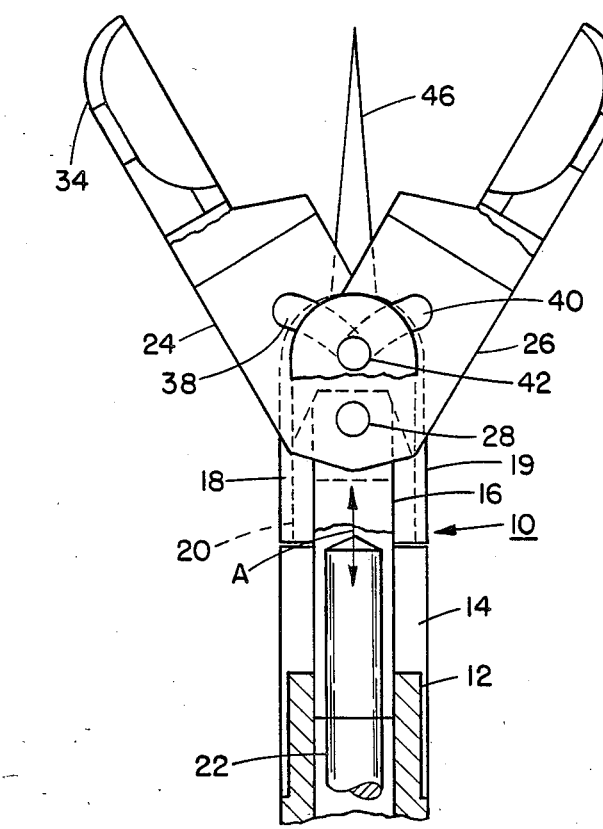
FIG. 1 illustrates, generally diagrammatically, a first embodiment of the operating end of an endoscopic biopsy forceps device which is constructed pursuant to the invention, the forceps jaws thereof being shown in an opened condition.
Figure 2:
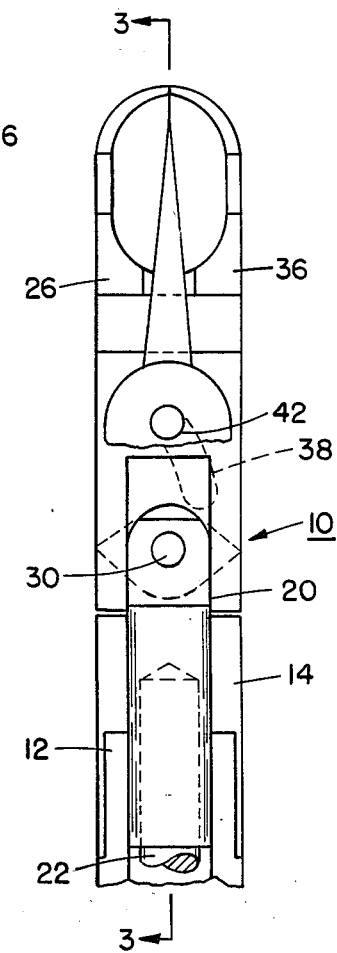
FIG. 2 illustrates the device of FIG. 1 with the clamping jaws of the forceps shown in a closed position.

Referring now in detail to FIGS. 1 to 3, there is illustrated the inventive endoscopic biopsy forceps device 10 which includes a forceps sheath 12 constituted of a generally flexible or pliable material; for instance, teflon tubing or the like, which is connected at a distal end thereof to a suitable operating mechanism (not shown) for actuating the forceps jaw structure of the biopsy forceps device.

Attached to the illustrated end of the sheath 12 is a suitable forceps lever support housing 14, which, if desired, may be constituted of stainless steel, and which includes a longitudinal central slot 16 fully extending between two opposite halves 18 and 19 of the housing 14. A slide member 20 is slidably supported for reciprocatory movement in the slot 16 in coaxial relationship with the flexible sheath 12. The slide member 20 has one end thereof fastened to a flexible cable or wire 22 which is telescopingly movable within the sheath 12 in response to operation of the endoscope operating mechanism (not shown), as is well known in this technology.

A pair of cooperating forceps levers 24 and 26 are articulated to the slide member 20 through the intermediary of pivots 28 and 30, as shown in more extensive detail in FIGS. 2 and 3. The pivots may be integrally formed with or fastened to the slide member 20, whereby reciprocatory movement of the wire 22 within the sheath 12 in response to actuation thereof will cause the pivots 28 and 30 to be rotated within bores 29, 31 in the shank portions of the forceps levers while being axially displaced within the slot 16 of housing 14 along the directions of double-headed arrow A, depending upon whether the forceps devices is to be opened or closed. The articulation of the wire 22, which causes the displacement of pivots 28 and 30 along the directions of arrow A will cause the concurrent displacement of the shank ends of the forceps levers 24 and 26 which are hinged to the sides member 20 at these pivots. The pivots 28, 30, if desired, may also be formed or rivets for fastening the forceps levers to the slide member.

The camming action which is imparted to the forceps levers 24 and 26 in response to the actuation or movement of wire 22 within the sheath 12 so as to selectively open or close forceps clamping jaws 34 and 36 at the free ends of the forceps levers distant from pivots 28, 30, is effectuated through the intermediary of a novel camming arrangement provided for on the forceps levers 28, 30 incorporation with housing 14. This arrangement comprises cam tracks, in the form of an elongate arcuate slot 38 formed in lever 24 and a similar oppositely curved slot 40 in the other forceps lever 26, adapted to superimposed impart, as shown in detail in FIG. 1 of the drawings. A fixed or stationary pivot pin 42, extends transversely through the cam track slots 38, 40, and is preferably in the shape of a screw which has the leading end of the screw portion thereof threadingly arranged in a completely threaded hole 44 formed in one of the opposite halves 18 or 19 of the housing 14, and with the head end of the screw being recessed in the opposite housing half so as to have the screw (or pivot pin) extend across the slot 16.

Fastened to the slide 20 so as to extend axially from the slot 16 between the clamping jaws 34 and 36 on the forceps levers, is a suitable pointed spike element 46, for engaging tissue from a body cavity of a patient, which tissue is to be clamped off by the jaws of the forceps for purposes of biopsies, as is well-known in the art.

As may be ascertained from the foregoing, the axial displacement of the slide member 20 with the pivots 28, 30, and the resultant movement of the ends of forceps levers 24, 26 which are hinged thereto, causes the cam track slots 38, 40 to move relative to the fixed pin or screw 42 extending therethrough. Consequently, as the wire 22 is retracted in the sheath 12, pulling the sliding member 20 and pivots 28, 30 away from the fixed screw or pin 42, the slots 38, 40 are biased together by the presence of the screw in their ends towards the forceps jaws, as shown in FIG. 2, and the forceps jaws pivoted towards each other into clamping engagement. Conversely, the movement of slide member 20 in the opposite direction of arrow A, causes the slots 38, 40 to be moved along screw 42 into a position towards the lower ends of slots 38, 40 (as shown in FIG. 1), and pivots the forceps levers 24, 26 apart so as to open the forceps jaws 34, 36. In essence, all movement is effected relative to a single fixed and two displaceable pivot joints in the camming arrangement, rather than through the numerous pivots of the prior art devices.

The embodiment illustrated in FIG. 4 of the drawings in which all components similar to or identical with those in FIGS. 1 through 3 are designated with the same reference numerals, is merely modified with regard to the previous embodiment, in that the cam track slots 50 and 52 each have two continuous linear portions 50' and 50", and 52' and 52" angled with regard to each other in lieu of the curvilinear cam track configurations of the previous embodiment. The portions 50' and 52' of the cam track slots 50, 52 which are proximate the ends of the forceps jaws are angled so as to extend more acutely with or closer to the axial centerline of the slide member 20 and forceps levers 24, 26 such that, upon closing of the forceps jaws, any further displacement of the wire 22 tending to continue closing of the jaws will impart a greater biasing or clamping force to the cooperating jaws by the screw in the slots, thereby enhancing the clamping action or mechanical advantage in gripping any tissue between the jaws.

From the foregoing, it becomes readily apparent to one skilled in the art that the novel endoscopic biopsy forceps device is constituted of appreciably fewer and simpler parts than the devices which are currently being marketed, offering an enhanced degree of product reliability through the reduction of components, simplicity in design, operation and manufacture, which renders the entire device much less expensive and highly economical in comparison with currently employed devices, so as to adapt it for use as a "throw-away" unit.

Due to the inventive camming arrangement, wherein the opening and closing movement of the forceps levers and of the forceps jaws are improved, the advantages offered by the inventive structure resides in:

(a) the cutting plane of the forceps jaws being closer to that of a straight line in comparison with the curvilinear movement employed by prior art devices, which results in an improved cutting action during the separation of the desired specimen or tissue;

(b) during the closing of the forceps jaws, the specimen or tissue is prevented from slipping out of the cutting zone of the biopsy forceps;

(c) the production cost of the inventive endoscopic biopsy forceps device is considerably reduced due to the considerably fewer employed components and articulated parts, thereby also increasing its operational reliability and stability;

(d) the area provided for engaging the jaws in cutting the specimen or tissue is considerably larger than for conventional forceps;

(e) basically all rivets and linkages encountered in prior art forceps of this type have been eliminated, which simplifies the overall assembly and also reduces the necessary assembling time for the forceps device.

(f) the resultant shorter operating stroke provided for by the camming arrangement increases the radius of operation of the device and imparts better control and feel of the device to nurses, physicians or medical technicians handling the forceps;

(g) elimination of any danger to a patient caused by an infection through the subsequent use of a biopsy forceps device which may still be contaminated, in that the reduction in the cost thereof renders the device disposable as a "throw-away" after a single use, while nevertheless still being appreciably more cost-effective in contrast with currently utilized biopsy forceps devices.

While there has been shown and described what is considered to be preferred embodiments of the invention, is will, of course, be understood that various modifications and changes in form or detail could readily be made without departing from the spirit of the invention. It is therefore intended that the invention be not limited to the exact form than the whole of the invention herein disclosed as hereinafter claimed.

What is claimed is:

1. A biopsy forceps device which is insertable through an endoscope into a body cavity for the separation of tissue therefrom; said forceps device comprising a flexible tubular sheath; a housing member secured to one end of said sheath and having a slot extending therethrough; a wire extending coaxially within said sheath for telescoping movement relative thereof; a movable member slidably supported in the slot of said housing member and being fastened to said wire; a pair of forceps levers each having a shank portion said shank portions having opposite ends and an operating jaw extending from one end of said shank portion; means at the opposite end of each said shank portion of each said lever for articulating said forceps levers to said movable member, a cam track consisting of a slot formed in each shank portion intermediate the ends thereof; and a single stationary pivot means extending through said slot in each said lever shank portion and being fixedly connected to said housing member, each of said cam tracks having opposite surfaces of said shank slot movably guided along said stationary pivot means whereby axial displacement of said movable member relative to said housing member responsive to axial movement of said wire in said sheath causes said slots to move in camming surface contact along said stationary pivot means and to pivot said forceps levers into respective opening and clamping movements of the clamping jaws on said forceps levers.

2. A forceps device as claimed in claim 1, wherein said pivot means extending through said cam slots in said forceps levers comprises a screw member extending across the slot in said housing member and includes a threaded screw portion engaged in a threaded bore in said housing member.

3. A forceps device as claimed in claim 1, wherein said forceps levers are articulated to said link member by pivots on said movable member pivotally engaging into bores in the shank portions of said levers.

4. A forceps device as claimed in claim 3, wherein said pivots are integrally formed with said movable member.

5. A forceps device as claimed in claim 1, wherein said cam slots comprise elongate arcuate slots extending in oppositely curved orientations in each of said forceps levers.

6. A forceps device as claimed in claim 1, wherein said cam slots comprise elongate slots having first and second linear elongate slot portions angled relative to each other and extending in oppositely sloped orientations in each of said forceps levers for effectuating the respective opening and closing camming movements of said forceps jaws.

7. A forceps device as claimed in claim 6, wherein the portion of each of said linear slots proximate the jaws extends at a narrow angle relative to the longitudinal axis of the forceps levers so as to increase the clamping action between said forceps jaws subsequent to this closing of said forceps.

* * * * *

UNITED STATES PATENT AND TRADEMARK OFFICE
CERTIFICATE OF CORRECTION

PATENT NO. : 4,887,612

DATED : December 19, 1989

INVENTOR(S) : Theodor Esser, et al.

It is certified that error appears in the above-identified patent and that said Letters Patent is hereby corrected as shown below:

Column 6, line 66, Claim 1: "portion said" should read as --portion, said--

Signed and Sealed this

Nineteenth Day of February, 1991

*Attest:*

HARRY F. MANBECK, JR.

*Attesting Officer*    *Commissioner of Patents and Trademarks*